United States Patent [19]
Bignell

[11] Patent Number: 5,832,817
[45] Date of Patent: Nov. 10, 1998

[54] CONSTANT PRESSURE PAPER PRESS

[76] Inventor: George Bignell, P.O. Box 389, Savona, British Columbia, Canada, V0K 2J0

[21] Appl. No.: 540,256

[22] Filed: Oct. 6, 1995

[30] Foreign Application Priority Data

Mar. 1, 1995 [CA] Canada ................................. 2143880

[51] Int. Cl.$^6$ .................................................. B30B 15/22
[52] U.S. Cl. ................................ 100/51; 73/825; 100/99; 100/229 R
[58] Field of Search ................................. 100/50, 51, 99, 100/194, 196, 229 R, 269.14, 269.15, 269.16; 73/818, 821, 825

[56] References Cited

U.S. PATENT DOCUMENTS

| 729,733 | 6/1903 | Carey .................................. 100/229 R |
| 2,191,687 | 2/1940 | Skates ................................. 100/229 R |
| 2,224,248 | 12/1940 | Blum et al. .............................. 100/99 |
| 2,245,080 | 6/1941 | Pendleton ................................. 100/99 |
| 2,720,331 | 10/1955 | Adshead .................................. 100/51 |
| 2,782,710 | 2/1957 | Fishburne ............................ 100/229 R |
| 3,454,741 | 7/1969 | Stewart . | |
| 4,554,868 | 11/1985 | Zimmer ............................... 100/229 R |

FOREIGN PATENT DOCUMENTS

| 77797 | 7/1949 | Czechoslovakia ................. 100/229 R |
| 2263473 | 7/1974 | Germany ........................... 100/229 R |
| 52-46880 | 4/1977 | Japan ....................................... 73/818 |
| 211863 | 4/1968 | U.S.S.R. ................................. 73/825 |

*Primary Examiner*—Stephen F. Gerrity
*Attorney, Agent, or Firm*—Bishop & Company

[57] ABSTRACT

A paper sample press has a drawer slidably mounted on a base. A plurality of generally vertical guide posts are mounted on the base on opposed sides of the drawer. The drawer has a lower platen mounted thereon for supporting a stack of paper samples. The drawer is slidable on the base from a retracted position between the guide posts to an extended position wherein the lower platen is extended out from between the guide posts, and returnably slidable on the base from the extended position to the retracted position. A vertically selectively actuable press cover is vertically mounted on a piston above the lower platen when the drawer is in the retracted position. The piston is selectively actuable so as to selectively lower and elevate the press cover between a raised position and a lowered paper sample engaging position. The paper sample press has piston support and a selective actuation device for supporting and selectively actuating the piston vertically over the lower platen so as to vertically selectively translate the press cover along a vertical press axis aligned with the lower platen between the raised position and the lowered paper sample engaging position. The piston support and selective actuation means is mounted on the guide posts. A constant compression device is provided for applying a generally constant compression pressure along the vertical press axis to a stack of paper samples placed on the lower platen when the drawer is in the retracted position and the press cover is in the lowered paper sample engaging position.

3 Claims, 4 Drawing Sheets

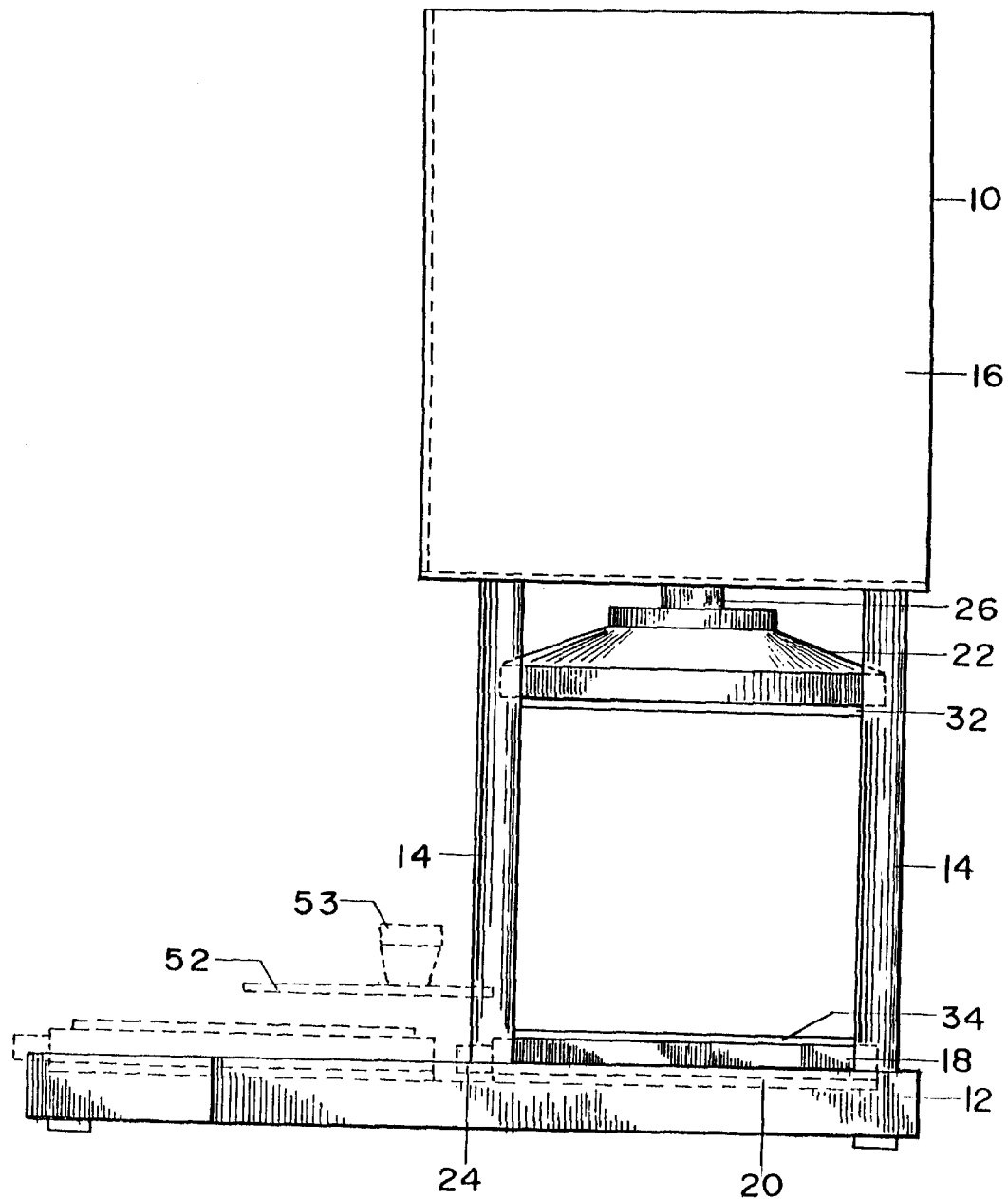

CONSTANT PRESSURE PAPER PRESS

FIELD OF THE INVENTION

The present invention relates to the field of pulp and paper and in particular to devices for pressing paper samples for testing.

BACKGROUND OF THE INVENTION

An example of a fundamental property of paper which is required to be tested is the paper's specific gravity. Testing specific gravity requires measuring the paper weight per unit area and the paper thickness. To determine the weight, a sample is brought to equilibrium under standard conditions since the properties of paper change with moisture content. By convention the paper specimens must consist of at least 10 sheets with a total area of not less than 100 square inches. The thickness of the paper samples is conventionally measured by placing a single sheet under a steady pressure of 7 to 9 pounds per square inch between two circular and parallel plain surfaces. The specific gravity of the paper is then calculated from the weight and the thickness. In order to perform such testing paper samples must be prepared. The method of preparation is governed by convention and involves compressing a paper sample according to specific time and pressure profiles.

In the prior art, the conventional paper presses used to prepare paper samples for testing typically press, in one run, 8 sheets of paper samples. Interspersed between the sheets are typically steel plates. Alignment is critical to proper pressing. Further, conventional paper presses have hydraulic or pneumatic ram cylinders which operate vertically from below the paper stack and would typically only have operational travel displacements of approximately $\frac{3}{8}$'s of an inch. These prior art presses are not usually constant pressure presses, meaning that they do not maintain a constant pressure over the $\frac{3}{8}$'s inch displacement of the ram cylinder. A requirement of the method according to the preparation convention of the Canadian Pulp and Paper Association is that pressing be at constant pressure.

In particular, using a conventional sheet paper press, the procedure involves, for a first pressing, placing the cover of the press evenly on the stack of sheets and alternatively screwing each nut of diagonal pairs of nuts down hand tight on the vertically protruding bolts protruding upwards from the base of the press. Once the cover is thus positioned, the pressure, as indicated by a gauge on the sheet press, is elevated to 50 pounds per square inch. This pressure is to be attained within 30 seconds from first indication of a registrable pressure on the gauge and once 50 pounds is obtained, the pressure is to be maintained for 5 minutes after which time the pressure is released and the press cover removed. The pressure of 50 pounds per square inch should be accurately controlled and maintained during pressing.

For a second pressing, the order of the sheets in the stack being pressed is reversed, the press cover replaced as before, and the pressure raised rapidly to 50 pounds per square inch and maintained for two minutes.

The necessity to fix a time period during the first pressing for obtaining the stipulated pressure of 50 pounds per square inch it is necessary to fix a time period for obtaining that pressure as there is a tendency noted in the prior art for the pressure to fall off. It is to address this pressure fall off that the constant pressure achieved by the present invention is advantageous.

In the prior art a template is used for centring the stack of sheets on the press.

Also in the prior art, Applicant is aware of the following United States patents which, although do not disclose devices and methods for forming paper samples for physical tests of pulp, do disclose testing equipment for testing the crushing resistance of paper and paperboard: U.S. Pat. No. 1,445,963 which issued to La Batt et al on Feb. 20, 1923 for a Testing Machine, and U.S. Pat. No. 2,224,248 which issued to Blum et al on Dec. 10, 1940 for an Apparatus for Testing the Crush Strength of Paper. Both references disclose compression testers for paper. Applicant notes that neither of these patents suggest a lower platen drawer moveable out of and into alignment with a pneumatically driven ram. La Batt teaches a machine for testing the crushing strength or resistance of corrugated paperboard in which liquid under pressure is exerted against an elastic diaphragm acting in a transverse direction against a confined section or area of testing stock. Blum teaches a device for measuring the crush strength of corrugated paper or the like by means of a small and compact instrument having a fluid pressure responsive cylinder, the cylinder preferably adapted to contain oil as its pressure transmitting medium. Pressure is applied by a hand screw and transmitted through the test stock and pressure transmitted medium in the cylinder so as to register a pressure on a gauge communicating with the cylinder.

Consequently, it is an object of the present invention to provide a constant pressure paper press in which alignment of paper sample sheets and steel plates is more easily obtained than in the prior art, the device capable of pressing a larger number of sheets of paper samples than may conventionally be pressed in one run in the prior art.

SUMMARY OF THE INVENTION

The constant pressure paper press of the present invention allows for ease of loading and ease of accurate alignment of a stack of paper samples being pressed, and also allows for up to 25 to 30 sheets of paper samples to be pressed during one pressing run.

Ease of loading and ease of alignment of the paper samples is achieved by a sliding drawer which slides from a retracted position to an extended position out from underneath a vertically aligned pneumatic ram operating from above the stack of paper samples. The paper samples to be pressed are placed on the sliding drawer in its extended position with steel plates interspersed between the samples. The steel plates and paper samples are aligned so as to be slid between vertically extending guide posts on either side of the sliding drawer, for example, by use of an alignment template, when the drawer is slid back into its retracted position vertically aligned under the pneumatic ram. Ease of alignment reduces the press cycle time for each stack of paper samples.

Increased capacity per pressing run is accomplished, in addition to the method of alignment, by means of a vertical ram maintaining a constant pressure on the stack of paper samples throughout the pressing cycle. A pneumatic ram supplying a constant pressure throughout the travel of the vertical ram thereby allows the pressing of a larger stack of samples, the guide posts assisting maintaining alignment of the larger stack of paper samples.

In operation, paper samples, otherwise referred to as hand sheets, are loaded onto the sliding drawer, otherwise referred to as the press platen drawer, when it is fully in the extended position, that is, when fully extended from beneath the press cover on the vertical pneumatic ram. The hand sheets are centred onto a press platen on the press platen drawer by means of a location template. The press platen drawer is then pushed fully back under the press cover into its retracted position so as to be vertically aligned underneath the press cover under the vertical pneumatic ram The press cover is then lowered on the vertical pneumatic ram so as to engage the lower surface of the press cover (which is also a press platen) with the top surface of the stack of hand sheets. Once the press cover has been settled on the stack of hand sheets so as to engage the upper press platen (being the lower surface of the press cover) against the top most surface of the stack of hand sheets, pneumatic pressure is applied to the pneumatic ram so as to compress the stack of hand sheets according to the standard method above described. During the constant pressure phase, above described as 50 pounds per square inch for 5 minutes during a first pressing, the pressure is regulated so as to maintain the desired constant pressure by means of further vertical translation of the pneumatic ram so as to maintain constant regulated air pressure. In one preferred embodiment on completion of the timed constant pressure phase, the pressure is automatically released and upon completion of this pressing sequence, the press cover opened automatically so as to allow the removal of the stack of hand sheets.

Ease and efficiency of centring the stack of hand sheets on the lower press platen is facilitated by a location template which may be quickly centred between a plurality of parallel posts extending between a base on which the press platen drawer is slidably mounted and a housing mounted on the parallel posts containing the pneumatic ram actuating and regulating apparatus.

BRIEF DESCRIPTION OF THE DRAWINGS

FIG. 2 is a side elevation view of the sheet press of FIG. 1.

FIG. 3b is a side elevation view of the press platen drawer of FIG. 3a.

FIG. 3c is an end elevation view of the press platen drawer of FIG. 3a.

DETAILED DESCRIPTION OF THE PREFERRED EMBODIMENT

Figure 1:
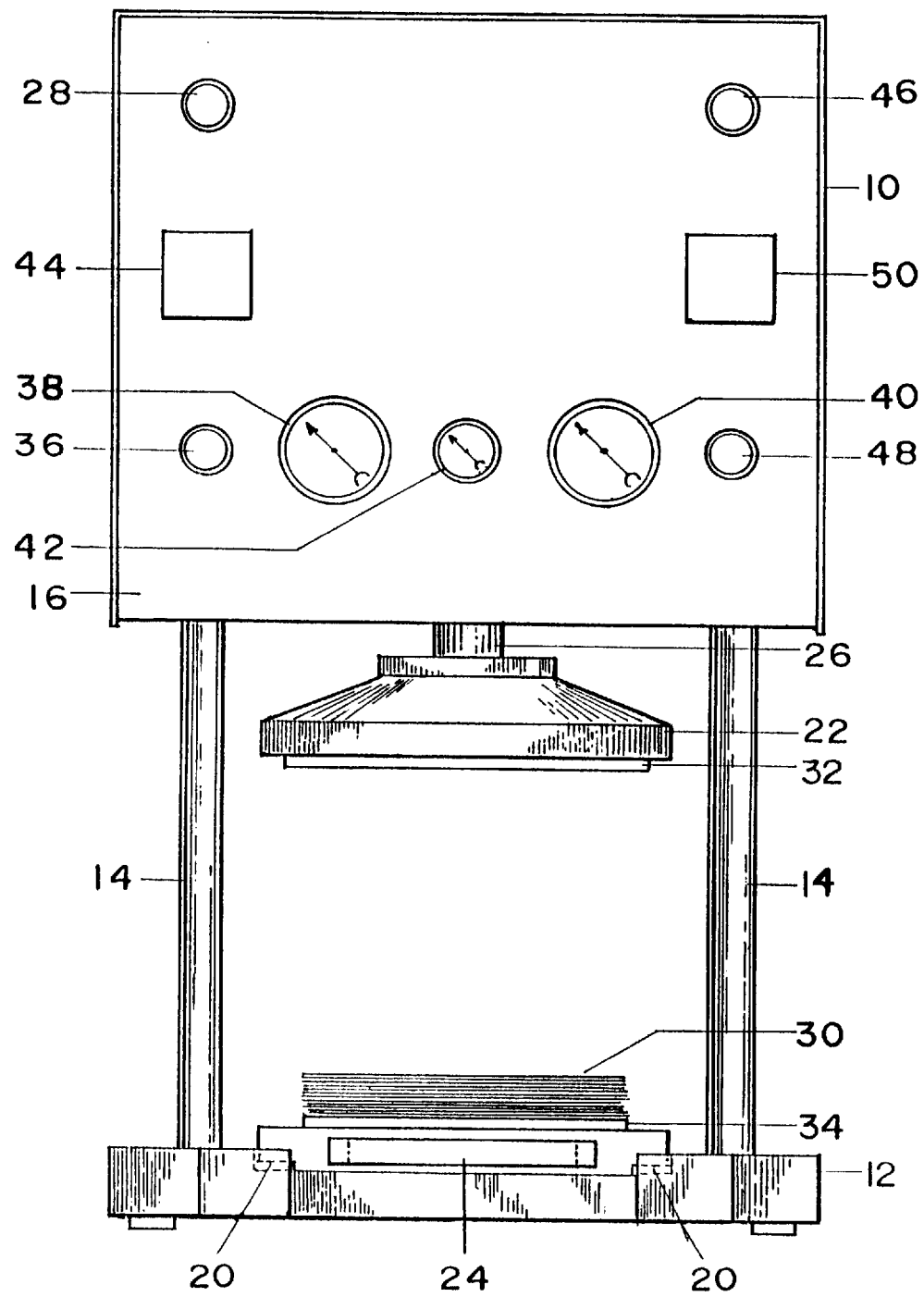
FIG. 1 is a front elevation view of the sheet press of the present invention.
Figure 3A:
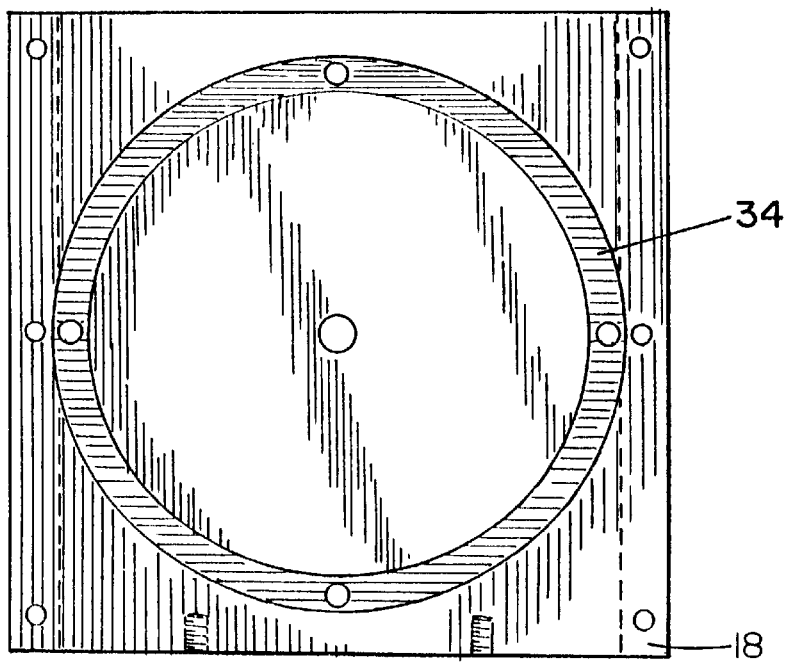
FIG. 3a is a top plan view of the press platen drawer of the sheet press of the present invention.
Figure 3B:
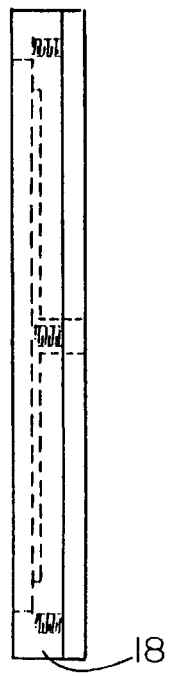
Figure 3C:
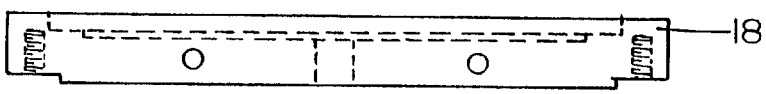
Figure 3D:
FIG. 3d is a top plan view of a drawer guide of the sheet press of the present invention.
Figure 3E:
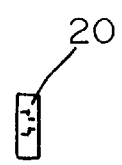
FIG. 3e is an end elevation view of the drawer guide of FIG. 3d.
Figure 3F:
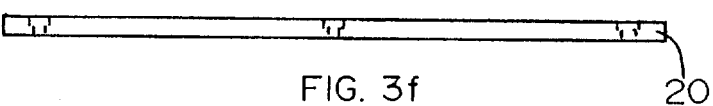
FIG. 3f is a side elevation view of the drawer guide of FIG. 3d.
Figure 4:
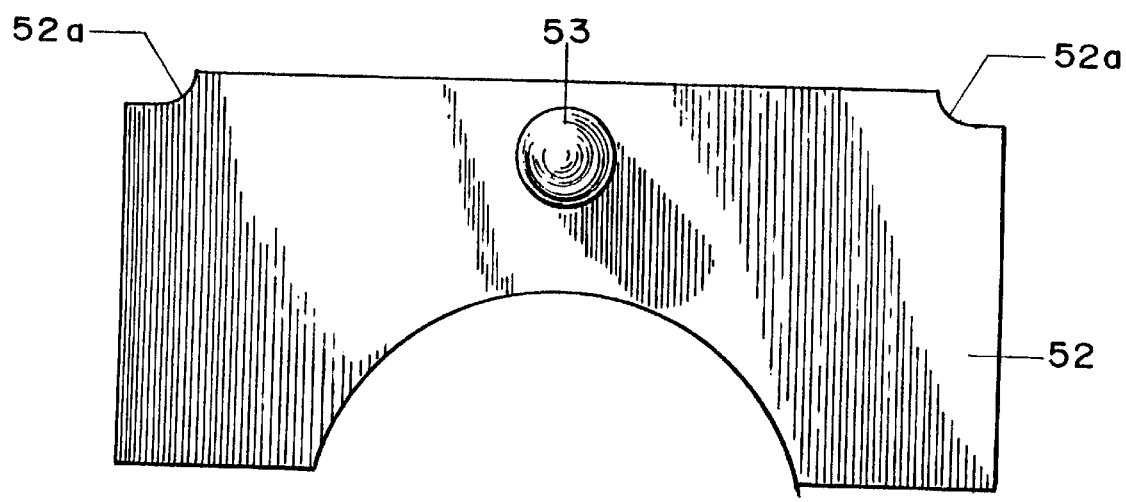
FIG. 4 is a top plan view of a location template used in the method of sheet pressing of the present invention.

As illustrated in FIG. 1, sheet press 10 has base 12 on which are vertically mounted guide posts 14 supporting thereupon housing 16. Press platen drawer 18 is slidably mounted on base 12 by means of an opposed pair of parallel TEFLON™ (polytetrafluoroethene) drawer guides 20 mounted to base 12.

As seen in FIG. 2, press platen drawer 18 may be advanced from a retracted position directly beneath press cover 22 by being slid on drawer guides 20 along the length of base 12 to an extended position illustrated in dotted outline. To facilitate movement of press platen drawer 18 on base 12, press platen drawer 18 may be provided with handle 24.

Housing 16 contains conventional air regulating apparatus for selectively applying pneumatic pressure to pneumatic ram cylinder 26 mounted to press cover 22. In the preferred embodiment, the pneumatic control apparatus contained within housing 16 comprises a first press cover closing mechanism activated by button 28 which acts to lower press cover 22 on pneumatic ram cylinder 26 so as to engage a stack of hand sheets between upper press platen 32 and lower press platen 34.

Once press cover 22 has been settled onto hand sheets 30, a first press sequence is activated by means of button 36 activating pressure regulating apparatus indicated in FIG. 1 by line pressure gauge 38 and regulated pressure gauge 40. The pressure regulating apparatus indicated diagrammatically at 42, regulates the pressure profile over time as the desired time is tracked by a first press timer illustrated diagrammatically at 44. Thus as described above, if the desired constant pressure during the first press sequence is 50 pounds per square inch, then the pressure regulator 42 acts to increase the compression force of upper press platen 32 acting so as to compress hand sheets 30 against lower press platen 34 by means of pneumatically extending pneumatic ram cylinder 26 until the regulated pressure of 50 pounds per square inch is obtained. This pressure is achieved within 30 seconds as monitored by first press timer 44 and then maintained for 5 minutes as also monitored by first press timer 44 after which time the regulated pressure is released and press cover 22 elevated by retracting pneumatic ram cylinder 26 into housing 16.

A second press sequence is activated and regulated by a second corresponding press cover closing mechanism activated by button 46, and a second press sequence activated by button 48 so as to follow a timed pressure profile according to second press timer 50 as regulated by pressure regulator 42.

In operation, hand sheets 30 are loaded onto lower press platen 34 when press platen drawer 18 is in its extended position on base 12, that is, when slid along base 12 on drawer guides 20 out from underneath press cover 22. Location template 52 is installed by means of handle 53 so as to snugly fit between guide posts 14. Guide posts 14 fit into recessed corners 52a. Thus with hand sheets 30 on lower press platen 34 aligned by means of location template 52, hand sheets 30 will, upon translation of press platen drawer 18 into its retracted position, be vertically aligned beneath press cover 22, ie. hand sheets 30 will be correctly aligned beneath upper press platen 32.

With hand sheets 30 properly aligned on lower press platen 34 and press platen drawer 18 in its retracted position, location template 52 is removed and button 28 pressed so as to lower press cover 22 on pneumatic ram cylinder 26 so as to engage upper press platen 32 against the uppermost surface of hand sheets 30. Once upper press platen 32 has settled onto hand sheets 30, button 36 is pressed to activate the first press sequence thereby bringing, for example, the vertical compression pressure applied to hand sheets 30 up to 50 pounds per square inch within 30 seconds and thereafter maintained at that pressure for 5 minutes before being released and upper press platen 32 being retracted by raising press cover 22.

If a second press sequence is desired, buttons 46 and 48 are sequentially pressed to once again to lower press cover 22 and initiate the second press sequence respectively.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A paper sample press comprising:

a drawer slidably mounted on a base, a plurality of generally vertical guide posts mounted on said base on opposed sides of said drawer, said drawer having a lower platen mounted thereon for supporting a stack of paper samples, said drawer slidable on said base from a retracted position between said guide posts to an extended position wherein said lower platen is extended out from between said guide posts, and returnable slidable on said base from said extended position to said retracted position, a vertically selectively actuable press cover vertically mounted on a piston above said lower platen when said drawer is in said retracted position, said piston selectively actuable so as to selectively lower and elevate said press cover between a raised position and a lowered paper sample engaging position, piston support and selective actuation means for supporting and selectively actuating said piston vertically over said lower platen so as to vertically selectively translate said press cover along a vertical press axis aligned with said lower platen between said raised position and said lowered paper sample engaging position, said piston support and selective actuation means mounted on said guide posts.

constant compression means for applying a generally constant compression pressure along said vertical press axis to a stack of paper samples placed on said lower platen when said drawer is in said retracted position and said press cover is in said lowered paper sample engaging position, wherein said constant compression means comprises means for applying a constant pressure to said piston along said vertical pressure axis, wherein said means for applying a constant pressure to said piston comprises pneumatic compression means for pneumatically translating and selectively controllably biasing said piston along said vertical press axis against said stack of paper samples, and further comprising pressure timing means for regulating a time and pressure profile of said generally constant compression pressure.

2. The device of claim 1 wherein said piston support and selective actuation means, are contained within a housing mounted on said guide posts, and said pneumatic compression means comprises means for applying a regulated pneumatic pressure to said piston support and selective actuation means so as to bias said piston and said press cover in said lowered paper sampling engaging position against said stack of paper samples on said lower platen.

3. The device of claim 2 wherein said pressure timing means further comprises first pressure timing means for regulating a first time and pressure profile whereby said press cover in said lowered paper sampling engaging position is biased vertically downwards against a stack of paper samples on said lower platen so as to provide a generally increasing compression pressure and obtain a first reference generally constant compression pressure within a first reference timed interval, and second pressure timing means for regulating a second time and pressure profile whereby said first reference generally constant compression pressure is maintained for a second reference time interval.

* * * * *